United States Patent [19]

Snader et al.

[11] 4,025,642
[45] May 24, 1977

[54] SUBSTITUTED 2H-PYRAN-2, 6(3H)-DIONE DERIVATIVES

[75] Inventors: Kenneth M. Snader, Hatboro, Pa.; Chester R. Willis, Kingston, Jamaica

[73] Assignee: SmithKline Corporation, Philadelphia, Pa.

[22] Filed: Dec. 3, 1975

[21] Appl. No.: 637,428

[52] U.S. Cl. .............................. 424/283; 260/343.5; 260/345.9
[51] Int. Cl.² ................ A61K 31/35; C07D 309/20
[58] Field of Search ................. 424/283; 260/345.9

[56] References Cited
UNITED STATES PATENTS

| | | | |
|---|---|---|---|
| 3,864,493 | 2/1975 | Cairns et al. | 424/283 |
| 3,879,544 | 4/1975 | Reisner et al. | 424/337 |
| 3,883,653 | 5/1975 | Barth | 424/251 |
| 3,885,038 | 5/1975 | Pfister et al. | 424/283 |

OTHER PUBLICATIONS

Wiley et al., J. Org. Chem. 21:686–688, (1956).
Kiang et al., J. Chem. Soc. (c) 2721–2726, (1971).

*Primary Examiner*—Norman A. Drezin
*Attorney, Agent, or Firm*—Richard D. Foggio; William H. Edgerton

[57] ABSTRACT

Substituted 2$\underline{H}$-pyran-2,6(3$\underline{H}$)-dione derivatives useful in the treatment of allergic conditions are prepared by reaction of 3,5-diacetyl-4,6-dihydroxy-2$\underline{H}$-pyran-2-one with an appropriate aniline.

24 Claims, No Drawings

SUBSTITUTED 2H-PYRAN-2, 6(3H)-DIONE DERIVATIVES

This invention relates to substituted 2H-pyran-2,6(3H)-dione derivatives which are useful for inhibiting the symptoms of an allergic response resulting from an antigen-antibody reaction. More specifically, the compounds of this invention are believed to be effective by inhibiting the release and/or formation and release of pharmacologically active mediators such as histamine, serotonin and slow-reacting substance of anaphylaxis (SRS-A) from effector cells which are produced and/or released as a result of an interaction of antigen and specific antibody fixed to the cell surface (allergic reaction). These properties make the subject compounds particularly useful in the treatment of various allergic diseases such as asthma, rhinitis and urticaria.

The compounds of this invention are represented by the following general structural formula:

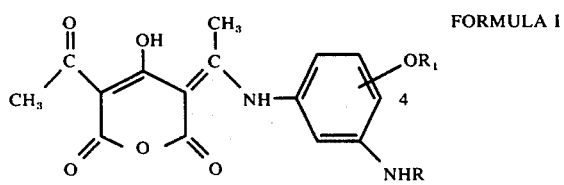

FORMULA I wherein:
R represents hydrogen or alkanoyl, straight or branched chain, of from 2 to 5 carbon atoms; and
$R_1$ represents hydrogen or lower alkyl of from 1 to 4 carbon atoms, preferably methyl.

The advantageous compounds of this invention are represented by formula I when the $OR_1$ substituent is in the 4-position and $R_1$ is hydrogen.

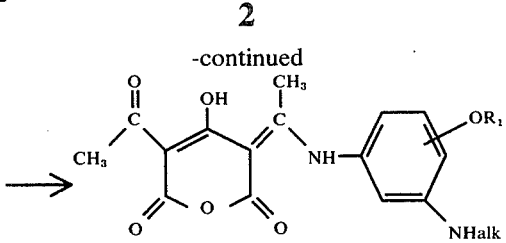

in which alk is alkanoyl, straight or branched chain, of from 2 to 5 carbon atoms and $R_1$ is hydrogen or lower alkyl of from 1 to 4 carbon atoms. Thus, 3,5-diacetyl-4,6-dihydroxy-2H-pyran-2-one and the appropriately substituted aniline are heated at reflux in an inert organic solvent such as benzene, toluene or methanol for from one to 12 hours to give the products.

To prepare the compounds of formula I wherein R is hydrogen, a substituted 3-nitroaniline is reacted as above with the pyran-2-one to give the corresponding nitro substituted derivative which is hydrogenated catalytically with palladium-on-carbon to obtain the free amino products.

Mono- and di-alkali metal salts of the compounds of formula I, such as the mono- and di-sodium or potassium salts are readily obtainable by treatment with the appropriate alkali metal alkoxide, for example methoxide, in an alkanol solvent such as methanol. Similarly, the free amino products (R is hydrogen) may be used in the form of a pharmaceutically acceptable acid addition salt, for example, those formed with either an inorganic or organic acid such as maleic, fumaric, methanesulfonic, acetic, hydrochloric, hydrobromic or sulfuric acids.

The pyran-2-one starting material indicated above is obtained by reaction by acetonedicarboxylic acid with acetic anhydride in sulfuric acid at elevated temperature. The reaction product actually has the tautomeric structure as shown below:

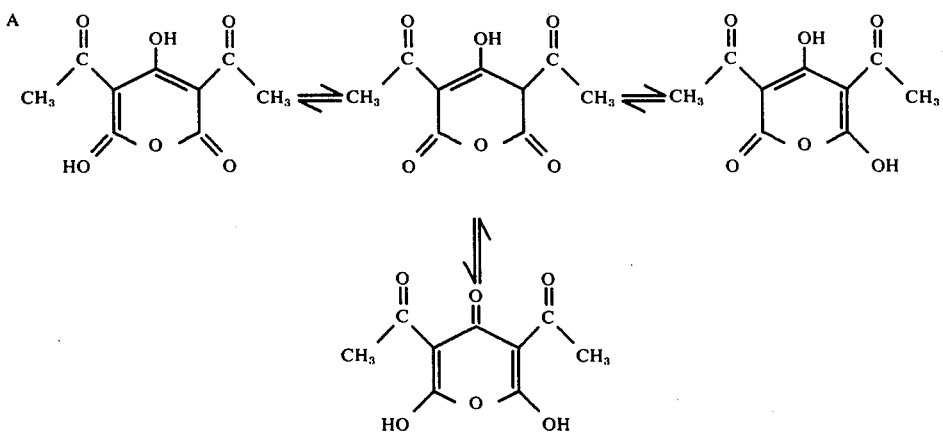

The compounds of formula I wherein R is alkanoyl are prepared as shown in the following scheme:

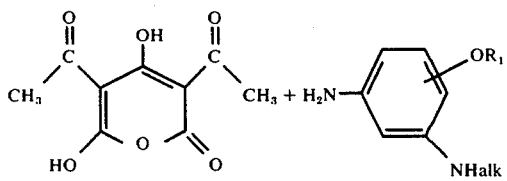

however for convenience it is designated herein as 3,5-diacetyl-4,6-dihydroxy-2H-pyran-2-one. Accordingly the reaction of this product with an aniline as shown above gives a product having the tautomeric structures as shown below:

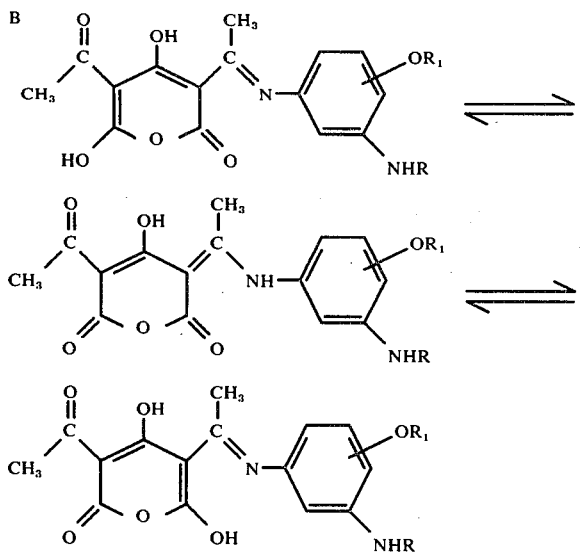

in which R and $R_1$ are as defined above for formula I. For convenience we have chosen to use one tautomeric form, namely the intermediate enamine pyran-2,6-dione structure, to represent all of the compounds formed by reaction of (A) with the aniline, as indicated by formula I above. It will be apparent however to one skilled in the art that the more complete representation of the compounds of formula I is shown by the tautomerization (B).

The alkanamido substituted aniline starting materials used herein are conveniently prepared by acylation of the appropriate nitroaniline followed by reduction of the nitro group to the aniline.

Wiley, R. H. et al. *J. Org. Chem.* 21:686–688 (1956) has reported the reaction of amines with the reaction product of acetonedicarboxylic acid and acetic anhydride, the latter designated 5-carboxydehydroacetic acid. Similarly, Kiang, A. K. et al. *J. Chem. Soc.* (c) pp. 2721-6 (1971) has disclosed such reaction products with amines. However there is no disclosure of products represented by formula I.

The inhibitory activity of the compounds of this invention on mediator release in sensitized tissues, thereby inhibiting the effects of the allergic reaction, is measured by the ability of the test compound to inhibit the passive cutaneous anaphylaxis (PCA) reaction in rats. In this test system, titered and appropriately diluted serum (from rats previously immunized by the intraperitoneal injection of ovalbuminaluminum hydroxide or ovalbumin-i.m.-Bordatella pertussis U.S.P. i.p.-and N-Brasiliensis i.p.) containing reaginic antibodies directed against ovalbumin is injected intradermally at four sites on the shaved backs of normal adult male rats. 48 hours later the animals are injected intravenously with 0.5 ml. of isotonic saline solution containing 5 mg. of the ovalbumin antigen and 5 mg. of Evans blue dye. Chemical mediators such as histamine and serotonin which are released at the sensitized sites as a result of a local cellular anaphylaxis, cause an increase in capillary permeability with resultant leakage of plasma and formation of a wheal. The wheal is visualized by the plasma protein-bound Evans blue dye. Under conditions of the test, the average control wheal is approximately 12×12 mm. 30 minutes following antigen challenge, the animals are killed, the dorsal skin is reflected and the diameter of the wheals recorded. A test compound is administered intravenously, initially at 0.5 minutes prior to antigen challenge (longer pretreatment times and other routes of drug administration, i.e. oral or intraperitoneal, may be employed). Percent inhibition is calculated from the difference in mean average wheal diameter between a treated group and saline or appropriate diluent controls.

The interruption by a test compound of the sequence of events triggered by reaginic antibody-antigen interaction of the surface of sensitized cells is indicative of utility in inhibiting the symptoms which result from an immediate-type allergic response.

The compounds of formula I administered intravenously to rats at doses of from 0.1 to 10 mg/kg produce marked inhibition of the PCA reaction. For example, 5-acetyl-3-[1-(3-amino-4-hydroxyphenylamino)ethylidene]-4-hydroxy-2H-pyran-2,6(3H)-dione produced 64% inhibition of the rat PCA wheal at 0.5 mg/kg, i.v. Another compound, 3-[1-(3-acetamido-4-hydroxyphenylamino)ethylidene]-5-acetyl-4-hydroxy-2H-pyran-2,6(3H)-dione, produced 45% inhibition of the rat PCA wheal at 0.1 mg/kg, i.v. Similarly 5-acetyl-4-hydroxy-3-[1-(3-propionamido-4-hydroxyphenylamino)ethylidene]-2H-pyran-2,6(3H)-dione produced 44% inhibition of the rat PCA wheel at 0.5 mg/kg, i.v.

In testing for mechanism of action the compounds of formula I, following i.v. administration at the same dose and pretreatment time which exhibited significant inhibition of the rat 48-hour PCA reaction, do not provide comparable inhibition of wheals of equal severity produced in rats by the intracutaneous administration of histamine and serotonin.

Upon oral administration, 5-acetyl-3-[1-(3-amino-4-hydroxyphenylamino)ethylidene]-4-hydroxy-2H-pyran-2,6-(3H)-dione produced approximately 80–85% inhibition in the rat 48-hour PCA system at 12.6 mg/kg and a pretreatment time of 15 minutes. The compound 3-[1-(3-acetamido-4-hydroxyphenylamino)ethylidene]-5-acetyl-4-hydroxy-2H-pyran-2,6(3H)-dione produced 51% inhibition of the rat PCA wheal after oral administration of 25 mg/kg at a predetermined time of 15 minutes. Similarly 5-acetyl-4-hydroxy-3-[1-(3-propionamido-4-hydroxyphenylamino)ethylidene]-2H-pyran-2,6(3H)-dione upon oral administration produced 60% inhibition in the rat 48-hour PCA system at 1 mg/kg and a pretreatment time of 15 minutes.

The compounds of this invention may be administered in conventional pharmaceutical compositions comprising an appropriate amount of a compound of formula I in association with a pharmaceutical carrier or diluent. The nature of the composition and the pharmaceutical carrier or diluent will of course depend upon the intended route of administration, i.e. orally, parenterally or by inhalation. Preferably a compound is administered to an animal in a composition comprising an amount sufficient to produce an inhibition of the symptoms of an allergic response. When employed in this manner, the dosage of the composition is such that from 0.5 mg. to 600 mg. of active ingredient are administered at each administration. Advantageously equal doses will be administered 1 to 4 times daily with the daily dosage regimen being about 0.5 mg. to about 2400 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g. lactose, for administration from a powder inhalation device. In the above compositions, the amount of carrier or diluent will vary but preferably will be the major proportion of a suspension or solution of the active ingredient. When the diluent is a solid, it may be present in less, equal or greater amounts than the solid active ingredient.

A wide variety of other pharmaceutical forms can be employed. Thus, if a solid carrier is used the preparation can be tableted, placed in a hard gelatin capsule in powder or pellet form, or in the form of a troche or lozenge for oral administration. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul, or an aqueous or non-aqueous liquid suspension.

Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

The pharmaceutical preparations thus described are made following the conventional techniques of the pharmaceutical chemist involving mixing, granulating and compressing when necessary, or variously mixing and dissolving the ingredients as appropriate to the desired end product.

Included within the scope of this invention is the method of inhibiting the symptoms of an allergic response resulting from an antigen-antibody reaction which comprises administering to an animal a therapeutically effective amount for producing said inhibition of a compound of formula I, preferably in the form of a pharmaceutical composition. The administration may be carried out in dosage units at suitable intervals or in single doses as needed. Preferably the method of this invention is practiced when relief of allergic symptoms is specifically required, however, the method is also usefully carried out as continuous or prophylactic treatment. A particular application is a method of relieving or preventing allergic airway obstruction which comprises administering to an animal a therapeutically effective amount at suitable intervals. It is within the skill of the art to determine by routine experimentation the effective dosage to be administered from the dose range set forth above, taking into consideration such factors as the degree of severity of the allergic condition being treated, and so forth.

The following examples illustrate the preparation of compounds of formula I and their incorporation into pharmaceutical compositions and as such are not to be considered as limiting the invention set forth in the claims appended hereto.

EXAMPLE 1

A mixture of 10 g. (0.065 mol) of 2-amino-4-nitrophenol, 125 ml. of dry toluene and 25 ml. of glacial acetic acid is heated to affect solution. Acetic anhydride (7.57 g., 0.074 mol) is added dropwise over a period of 20 minutes and the resulting mixture is heated at about 80° C. for 2 hours. The reaction mixture is filtered and the solid is washed with toluene, then recrystallized from methanol to give 2-acetamido-4-nitrophenol, m.p. 283°–284° C.

The 2-acetamido-4-nitrophenol thus prepared (6.6 g., 0.034 mol) in 200 ml. of methanol and 5.65 ml. of concentrated hydrochloric acid is hydrogenated with 0.50 g. of 10% palladium-on-carbon in a Parr apparatus for about 1 hour. The reaction mixture is filtered and the methanol removed in vacuo to yield 2-acetamido-4-aminophenol hydrochloride. The latter (4.8 g., 0.0236 mol) is dissolved in a minimum amount of methanol and treated with a solution of sodium bicarbonate (1.98 g., 0.0236 mol) in about 25 ml. of water. This solution is added to a solution of 5.0 g. (0.0236 mol) of 3,5-diacetyl-4,6-dihydroxy-2$\underline{H}$-pyran-2-one in refluxing methanol and refluxed for 2.5 hours under nitrogen. The resulting mixture is stirred at room temperature overnight and then filtered. The solid is washed with ether, boiled with a large excess of dioxane and filtered. The solvent is reduced to about 150 ml., 100 ml. of acetonitrile is added and after cooling overnight the product is obtained, 3-[1-(3-acetamido-4-hydroxyphenylamino)ethylidene]-5-acetyl-4-hydroxy-2$\underline{H}$-pyran-2,6(3$\underline{H}$)-dione, m.p. 248°–250° C. (dec.). Both the mono- and di-sodium salts are prepared upon treatment of the dione with sodium methoxide in methanol.

EXAMPLE 2

Following the procedure of Example 1, 3 g. (0.0195 mol) of 4-amino-2-nitrophenol is added to a refluxing solution of 4.1 g. (0.0195 mol) of 3,5-diacetyl-4,6-dihydroxy-2$\underline{H}$-pyran-2-one in methanol and the mixture is refluxed for about 2 hours. Filtration of the reaction mixture yields 5-acetyl-4-hydroxy-3-[1-(3-nitro-4-hydroxyphenylamino)ethylidene]-2$\underline{H}$-pyran-2,6(3$\underline{H}$)-dione, m.p. 236°–237° C. (dec.).

The nitroenamine (4.1 g., 0.0118 mol) is hydrogenated in a mixture of 200 ml. of ethanol and 0.4 g. of 10% palladium-on-carbon on a Parr apparatus at room temperature. The precipitate is filtered, dissolved in tetrahydrofuran and filtered again. The resulting solution is treated with ethereal hydrogen chloride to give 5-acetyl-3-[1-(3-amino-4-hydroxyphenylamino)ethylidene]-4-hydroxy-2$\underline{H}$-pyran-2,6(3$\underline{H}$)-dione hydrochloride, dec. > 240° C.

EXAMPLE 3

To a mixture of 82 ml. of dry toluene, 20 ml. of isobutyric acid and 5 g. (0.0324 mol) of 2-amino-4-nitrophenol is added 5.2 ml. of isobutyric anhydride. The resulting suspension is refluxed for 2 hours, filtered and the solid is air-dried overnight to give, 2-isobutyramido-4-nitrophenol, m.p. 239°–240° C. (dec.).

The nitrophenol prepared above (1.0 g., 0.0045 mol) is hydrogenated at room temperature in a mixture of ethanol and 10% palladium-on-carbon on a Parr apparatus until the calculated amount of hydrogen is absorbed. The catalyst is removed by filtration and the solvent evaporated in vacuo to leave 4-amino-2-isobutyramidophenol.

This phenol (0.86 g., 0.0045 mol) is refluxed with 3,5-diacetyl-4,6-dihydroxy-2H-pyran-2-one (0.96 g.) in 50 ml. of methanol for 10 hours. The reaction mixture is filtered and the solid is recrystallized from ethanol to furnish 5-acetyl-4-hydroxy-3-[1-(3-isobutyramido-4-hydroxyphenylamino)ethylidene]-2H-pyran-2,6(3H)-dione, m.p. 208°–209° C. (dec.).

EXAMPLE 4

Following the procedures of Example 1, 4.0 g. (0.0204 mol) of 4-acetamido-2-nitrophenol (prepared by acetylation of the corresponding amine) is hyrogenated in a mixture of 150 ml. of ethanol, 3.3 ml. of concentrated hydrochloric acid and 0.5 g. of 10% palladium-on-carbon in a Parr apparatus at room temperature. Filtration of the reaction mixture gives a powder which is dissolved in a minimum amount of water and filtered. This aqueous solution of 4-acetamido-2-aminophenol hydrochloride is added to a mixture of 3,5-diacetyl-4,6-dihydroxy-2H-pyran-2-one (3.42 g., 0.0162 mol) and 1.36 g. (0.0162 mol) of sodium bicarbonate in 130 ml. of methanol. After 18 hours at reflux, the reaction mixture is filtered and the solid is recrystallized from dioxane-acetonitrile to give 3-[1-(5-acetamido-2-hydroxyphenylamino)ethylidene]-5-acetyl-4-hydroxy-2H-pyran-2,6(3H)-dione, m.p. 253°–254° C. (dec.).

Similarly reaction of 5-acetamido-3-aminophenol hydrochloride with 3,5-diacetyl-4,6-dihydroxy-2H-pyran-2-one as described above furnishes 3-[1-(5-acetamido-3-hydroxyphenylamino)ethylidene]-5-acetyl-4-hydroxy-2H-pyran-2,6(3H)-dione.

EXAMPLE 5

Following the procedures of Example 3, 2.0 g. (0.0096 mol) of 4-nitro-2-propionamidophenyl (prepared from propionic acid and 2-amino-4-nitrophenyl) is hydrogenated in a mixture of 100 ml. of ethanol, 0.3 g. of 10% palladium-on-carbon and 1.34 ml. of concentrated hydrochloric acid in a Parr apparatus. Filtration and evaporation of the solvent gives 4-amino-2-propionamidophenol hydrochloride. The latter (2.0 g., 0.0096 mol) in a methanol solution is treated with 1 equivalent of triethylamine under nitrogen atmosphere. The solution of the free amine is added to a refluxing mixture of one equivalent of 3,5-diacetyl-4,6-dihydroxy-2H-pyran-2-one and 30 ml. of methanol under nitrogen. The reaction mixture is refluxed for 18 hours, filtered and the solid is recrystallized from ethanol to yield 5-acetyl-4-hydroxy-3-[1-(4-hydroxy-3-propionamidophenylamino)ethylidene]-2H-pyran-2,6(3H)-dione, m.p. 228°–229° C. (dec.).

EXAMPLE 6

Employing the procedures of Example 1, 1.0 g. (0.0048 mol) of 2-methoxy-5-nitroacetanilide (prepared by acetylation of the corresponding amine) is hydrogenated in 100 ml. of ethanol in the presence of 0.3 g. of 10% palladium-on-carbon in a Parr apparatus at room temperature. Filtration and evaporation of the solvent gives 3-acetamido-4-methoxyaniline.

The aniline thus prepared (0.8 g., 0.0045 mol) is added to a hot suspension of 3,5-diacetyl-4,6-dihydroxy-2H-pyran-2-one in 50 ml. of methanol. The mixture is refluxed for 1 hour and filtered to obtain 3-[1-(3-acetamido-4-methoxyphenylamino)ethylidene]-5-acetyl-4-hydroxy-2H-pyran-2,6(3H)-dione, m.p. 252°–253° C. (dec.).

As a specific embodiment of a useful composition of this invention, an active ingredient such as 3-[1-(3-acetamido-4-hydroxyphenylamino)ethylidene]-5-acetyl-4-hydroxy-2H-pyran-2,6(3H)-dione is dissolved in sterile water at a concentration of 0.5% and aerosolized from a nebulizer operating at an air flow adjusted to deliver the desired aerosolized weight of drug.

For oral administration, compositions such as those in the following examples can be prepared.

EXAMPLE 7

| Ingredients | Mg./Tablet |
|---|---|
| 5-Acetyl-3-[1-(3-amino-4-hydroxyphenylamino)ethylidene]-4-hydroxy-2H-pyran-2,6(3H)-dione (employed as the hydrochloride salt) | 10 |
| Calcium sulfate, dihydrate | 150 |
| Sucrose | 25 |
| Starch | 15 |
| Talc | 5 |
| Stearic acid | 3 |

The sucrose, calcium sulfate and active ingredient are thoroughly mixed and granulated with hot 10% gelatin solucation. The wetted mass is passed through a No. 6 mesh screen directly onto drying trays. The granules are dried at 120° F. and passed through a No. 20 mesh screen, mixed with the starch, talc and stearic acid, and compressed into tablets.

EXAMPLE 8

| Ingredients | Mg./Capsule |
|---|---|
| 5-Acetyl-4-Hydroxy-3-[1-(4-hydroxy-3-propionamidophenylamino)ethylidene]-2H-pyran-2,6(3H)-dione | 50 |
| Magnesium stearate | 5 |
| Lactose | 350 |

The above ingredients are screened through a No. 40 mesh screen, mixed and filled into No. 0 hard gelatin capsules.

What is claimed is:

1. A compound represented by the formula:

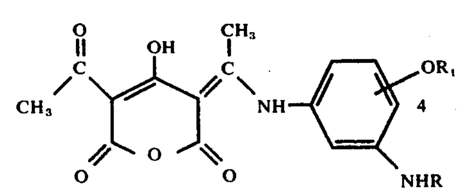

wherein:

R is hydrogen or alkanoyl, straight or branched chain, of from 2 to 5 carbon atoms; and $R_1$ is hydrogen or lower alkyl of from 1 to 4 carbon atoms, a mono- or di-alkali metal salt of said compound or a pharmaceutically acceptable acid addition salt of said compound when R is hydrogen.

2. A compound according to claim 1 in which $OR_1$ is in the 4-position.

3. A compound according to claim 2 in which $R_1$ is hydrogen.

4. A compound according to claim 3 in which R is hydrogen.

5. A compound according to claim 4 in the form of a hydrochloride salt.

6. A compound according to claim 3 in which R is acetamido.

7. A compound according to claim 3 in which R is propionamido.

8. A pharmaceutical composition for inhibiting the symptoms of asthma comprising a nontoxic pharmaceutical carrier or diluent and an amount sufficient to produce said inhibition of a compound represented by the formula:

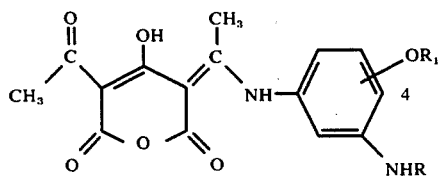

wherein:
R is hydrogen or alkanoyl, straight or branched chain, of from 2 to 5 carbon atoms; and
$R_1$ is hydrogen or lower alkyl of from 1 to 4 carbon atoms, a mono- or di-alkali metal salt of said compound or a pharmaceutically acceptable acid addition salt of said compound when R is hydrogen.

9. A pharmaceutical composition according to claim 8 in a form suitable for administration by inhalation.

10. A pharmaceutical composition according to claim 8 comprising a solution or suspension of the active ingredient in sterile water.

11. A pharmaceutical composition according to claim 8 in the form of an aerosol formulation.

12. A pharmaceutical composition according to claim 8 in which the pharmaceutical carrier or diluent is a solid.

13. A pharmaceutical composition according to claim 8 in which $OR_1$ is in the 4-position.

14. A pharmaceutical composition according to claim 13 in which $R_1$ is hydrogen.

15. A pharmacuetical composition according to claim 14 in which R is hydrogen.

16. A pharmaceutical composition according to claim 14 in which R is acetamido.

17. A pharmaceutical composition according to claim 14 in which R is propionamido.

18. A pharmaceutical composition according to claim 8 in which the active ingredient is in an amount of from about 0.5 mg. to about 600 mg. per dosage unit.

19. A pharmaceutical composition according to claim 18 in which $OR_1$ is in the 4-position, $R_1$ is hydrogen and R is hydrogen, acetamido or propionamido.

20. A pharmaceutical composition according to claim 19 in a form suitable for oral administration.

21. A pharmaceutical composition according to claim 20 in the form of a tablet or capsule.

22. The method of inhibiting the symptoms of asthma which comprises administering to an animal in need of said inhibition a therapeutically effective amount for producing said inhibition of a compound represented by the formula:

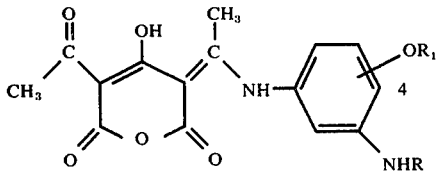

wherein:
R is hydrogen or alkanoyl, straight or branched chain, of from 2 to 5 carbon atoms; and
$R_1$ is hydrogen or lower alkyl of from 1 to 4 carbon atoms,
a mono- or di-alkali metal salt of said compound or a pharmaceutically acceptable acid addition salt of said compound when R is hydrogen.

23. The method according to claim 22 in which the active ingredient is administered in a daily dosage regimen of from about 0.5 mg. to about 2400 mg.

24. The method according to claim 22 in which $OR_1$ is in the 4-position, $R_1$ is hydrogen and R is hydrogen, acetamido or propionamido.

* * * * *

UNITED STATES PATENT AND TRADEMARK OFFICE
CERTIFICATE OF CORRECTION

PATENT NO. : 4,025,642
DATED : May 24, 1977
INVENTOR(S) : Kenneth M. Snader and Chester R. Willis It is certified that error appears in the above-identified patent and that said Letters Patent are hereby corrected as shown below:

Column 9, line 8 (Claim 6), "acetamido" should read ---acetyl---.

Column 9, line 10 (Claim 7), "propionamido" should read ---propionyl---.

Column 10, line 4 (Claim 16), "acetamido" should read ---acetyl---.

Column 10, line 6 (Claim 17), "propionamido" should read ---propionyl---.

Column 10, line 13 (Claim 19), "acetamido or propionamido" should read ---acetyl or propionyl---.

Column 10, line 45 (Claim 24), "acetamido or propionamido" should read ---acetyl or propionyl---.

Signed and Sealed this

Tenth Day of July 1979

[SEAL]

Attest:

*Attesting Officer*

LUTRELLE F. PARKER
*Acting Commissioner of Patents and Trademarks*